(12) United States Patent
Parthasaradhi Reddy et al.

(10) Patent No.: US 8,492,577 B2
(45) Date of Patent: Jul. 23, 2013

(54) PROCESS FOR PREPARATION OF VALSARTAN INTERMEDIATE

(75) Inventors: Bandi Parthasaradhi Reddy, Andhrapradesh (IN); Kura Rathnakar Reddy, Andhrapradesh (IN); Rapolu Raji Reddy, Andhrapradesh (IN); Dasari Muralidhara Reddy, Andhrapradesh (IN); Matta Ramakrishna Reddy, Andhrapradesh (IN)

(73) Assignee: Hetero Research Foundation (IN)

( * ) Notice: Subject to any disclaimer, the term of this patent is extended or adjusted under 35 U.S.C. 154(b) by 0 days.

(21) Appl. No.: 12/531,425

(22) PCT Filed: Apr. 7, 2008

(86) PCT No.: PCT/IN2008/000227
§ 371 (c)(1),
(2), (4) Date: Sep. 15, 2009

(87) PCT Pub. No.: WO2009/125416
PCT Pub. Date: Oct. 15, 2009

(65) Prior Publication Data
US 2011/0237822 A1      Sep. 29, 2011

(51) Int. Cl.
*C07C 253/30* (2006.01)
(52) U.S. Cl.
USPC .......................................... 558/414
(58) Field of Classification Search
None
See application file for complete search history.

(56) References Cited

U.S. PATENT DOCUMENTS

| 5,399,578 | A | 3/1995 | Buhlmayer et al. | |
| 6,271,375 | B1* | 8/2001 | Villa et al. | 544/279 |
| 7,741,507 | B2* | 6/2010 | Soni et al. | 558/425 |
| 7,923,567 | B2* | 4/2011 | Soni et al. | 548/253 |
| 7,943,794 | B2* | 5/2011 | Saxena et al. | 558/414 |
| 2006/0149079 | A1 | 7/2006 | Padi et al. | |
| 2006/0211866 | A1 | 9/2006 | Joshi et al. | |
| 2006/0258878 | A1* | 11/2006 | Soni et al. | 558/408 |
| 2006/0281801 | A1* | 12/2006 | Kumar et al. | 514/381 |
| 2009/0203921 | A1* | 8/2009 | Saxena et al. | 548/253 |

FOREIGN PATENT DOCUMENTS

| EP | 1714963 | 10/2006 |
| EP | 1777224 | 4/2007 |
| WO | WO2004111018 | 12/2004 |
| WO | WO2005021535 | 3/2005 |
| WO | WO2005049586 | 6/2005 |
| WO | WO2005102987 | 11/2005 |
| WO | WO2006058701 | 6/2006 |
| WO | WO2006067216 | 6/2006 |
| WO | WO2007005967 | 1/2007 |
| WO | WO2007006531 | 1/2007 |
| WO | WO2007032019 | 3/2007 |
| WO | WO2007045675 | 4/2007 |
| WO | WO2007054965 | 5/2007 |
| WO | WO2007057919 | 5/2007 |
| WO | WO2007071750 | 6/2007 |
| WO | WO2008004110 | 1/2008 |
| WO | WO2008007391 | 1/2008 |

OTHER PUBLICATIONS

Machine Translation of JP 11-322,697, Nov. 1999.*
Beutler, Ultrich et al. "A High-Throughput Process for Valsartan", Organic Process Research & Development , 11(5), 892-898, available online Jul. 28, 2007.*
Peter Buhlmayer, et al., Valsartan, a potent, orally active angiotensin II antagonist developed from the structurally new amino acid series, Bioorganic & Medicinal Chemistry Letters, vol. 4, No. 1, pp. 29-34, 1994.

* cited by examiner

*Primary Examiner* — Kamal Saeed
(74) *Attorney, Agent, or Firm* — Caesar, Rivise, Bernstein, Cohen & Pokotilow, Ltd.

(57) ABSTRACT

The present invention provides a process for preparation of a key intermediate of valsartan in a pure form and use of this intermediate for the preparation of valsartan or a pharmaceutically acceptable salt in pure form.

11 Claims, 2 Drawing Sheets

PROCESS FOR PREPARATION OF VALSARTAN INTERMEDIATE

FIELD OF THE INVENTION

The present invention provides a process for preparation of a key intermediate of valsartan in a pure form and use of this intermediate for the preparation of valsartan or a pharmaceutically acceptable salt in pure form.

BACKGROUND OF THE INVENTION

Valsartan, the generic name for N-(1-oxopentyl)-N-[[2'-(1H-tetrazol-5-yl)[1,1-biphenyl]-4-yl]methyl]-L-valine (denoted as formula I below) is a well known nonpeptide angiotensin II $AT_1$-receptor antagonist and is on the market as Diovan or Tareg for the treatment of hypertension.

According to U.S. Pat. No. 5,399,578 and Bioorganic & Medicinal Chemistry Letters, vol. 4, No. 1, pp. 29-34, 1994, valsartan is prepared by the following reaction steps.

L-valine methyl ester hydrochloride is N-alkylated with 4-bromomethyl-2'-cyanobiphenyl, the product 4-[(2'-cyanobiphenyl-4-yl)methyl]-(L)-valine methyl ester thus formed is N-acylated with valeryl chloride to give N-[(2'-cyanobiphenyl-4-yl)methyl]-N-valeryl-(L)-valine methyl ester. N-[(2'-cyanobiphenyl-4-yl)methyl]-N-valeryl-(L)-valine methyl ester is treated with tributyltin azide to give valsartan methyl ester, which is then hydrolyzed under alkaline condition to give finally valsartan.

4-[(2'-Cyanobiphenyl-4-yl)methyl]-(L)-valine methyl ester may also be prepared by reductive amination of 2'-cyanobiphenyl-4-carbaldehyde with L-valine methyl ester using sodium cyanoborohydride.

The above process requires chromatographic techniques to isolate/purify the intermediates, particularly those that are formed in N-alkylation, N-acylation and tetrazole formation steps.

Since it requires chromatographic separations in many stages, the above process is complicated in operation and large-scale equipment is required, which results in poor productivity. In view of these drawbacks, the above process can hardly be said to be an advantageous one from the industrial production viewpoint.

According to U.S. Pat. No. 5,399,578 and Bioorganic & Medicinal Chemistry Letters, vol. 4, No. 1, pp. 29-34, 1994, valsartan is also prepared by the following reaction steps.

L-valine benzyl ester hydrochloride is N-alkylated with 4-bromomethyl-2'-cyanobiphenyl, the product 4-[(2'-cyanobiphenyl-4-yl)methyl]-(L)-valine benzyl ester so formed is N-acylated with valeryl chloride to give N-[(2'-cyanobiphenyl-4-yl)methyl]-N-valeryl-(L)-valine benzyl ester. N-[2'-cyanobiphenyl-4-yl)methyl]-N-valeryl-(L)-valine benzyl ester is treated with tributyltin azide to give valsartan benzyl ester. Valsartan benzyl ester is subjected to catalytic hydrogenation using for example palladium-charcoal as catalyst to give valsartan.

According to WO 04111018 Valsartan is prepared by the hydrolysis of valsartan benzyl ester with an alkali metal hydroxide, washing with an organic solvent, acidifying with hydrochloric acid and isolating valsartan from the reaction mixture.

WO 2005/021535 provides a method of removing the trityl group from benzyl ester of trityl valsartan by solvolysis in anhydrous alcohol, which is deprived of excess of methyltriphenylether.

According to WO 2005/049586 valsartan is prepared by the reaction of L-valine methylester and 2N-trityl-5-(4'-bromomethylbiphenyl-2-yl)tetrazole followed by acylation with valeryl chloride to give N-pentanoyl-N-[[2'-(2N-trityl-tetrazole-5-yl)[1,1'-biphenyl]-4-yl]methyl]-L-valinemethylester. On removal of the trityl group under acidic conditions, valsartan methyl ester is obtained. valsartan methyl ester on reaction with metallic and ammonium trialkylsilanolates yields valsartan.

According to WO 2006/058701 A1 valsartan is prepared by the reaction of 5-(4-Bromomethyl)-biphenyl-2-yl)-1-(triphenylmethyl)tetrazole and L-valine methyl ester followed by acylation with valerylchloride and deprotection of the resulting compound to give valsartan. The product obtained by the reaction of 5-(4-Bromomethyl)-biphenyl-2-yl)-1-(triphenylmethyl)tetrazole and L-valine methyl ester is free of di alkylated product.

WO 2005/102987 provides the reaction of 4-Bromobenzylic bromide and hydrochloride methylester of L-valine methylester in an aprotic solvent and organic or an inorganic base to give methylester of N-(4-bromobenzyl)-L-valine which is deprotected to give N-(4-bromobenzyl)-L-valine. This on acylation with valeryl chloride yields N-(4-bromobenzyl)-N-valeryl-L-valine. Valsartan is prepared by the reaction of N-(4-bromobenzyl)-N-valeryl-L-valine and 2-(1H-tetrazole-5-yl)phenylboronic acid in palladiumtetrakistriphenylphosphine.

According to US 2006/0149079 A1 N-[(2'-cyanobiphenyl-4-yl)methyl]-(L)-valine methylester is acylated with valerylchloride in the presence of inorganic base to give N-[(2'-cyanobiphenyl-4-yl)methyl]-N-valeryl-(L)-valine methylester with valerylchloride, followed by the conversion of cyano to tetrazole and hydrolyzing the tetrazole derivative to obtain valsartan.

According to WO 2006/067216 valsartan is prepared by the condensation of valine derivative with phenylboronic acid derivative to give 4-valinylmethylphenyl boronic acid derivative, which is treated with halophenyl tetrazole in the presence of a metallic base, followed by the deprotection of tetrazole to give valsartan.

According to US 2006/0211866 A1 valsartan is prepared by the condensation of valine moiety and biphenyl derivative in the presence of a phase transfer catalyst in a biphasic solvent system.

According to EP 1714963 4-Bromomethyl-2'-cyanobiphenyl is condensed with L-valinebenzylester tosylate to give (S)-N-[(2'-cyanobiphenyl-4-yl]methyl]-(L)-valine benzylester hydrochloride. (S)-N-cyanobiphenyl-4-yl]methyl]-(L)-valine benzylester on reaction with valerylchloride yields (S)-N-cyanobiphenyl-4-yl]methyl]-N-valeryl-(L)-valine benzylester further by the reaction of tributyltin chloride and sodiumazide gives benzyl valsartan and debenzylation with Pd/C to give valsartan. Also discloses the process for the recovery of benzyl valsartan substantially free of organo tin impurity.

According to WO 2007/032019 A1 valsartan is prepared by the condensation of 4-halomethyl-2'-cyanobiphenyl with L-valine benzylester to give N-[(2'-cyanobiphenyl-4-yl]methyl]-(L)-valine ester derivative. N-[(2'-cyano biphenyl-4-yl]methyl]-(L)-valine ester derivative is treated with an organic acid to obtain the salt of N-[(2'-cyanobiphenyl-4-yl]methyl]-(L)-valine ester which is substantially free of dimeric impurity, followed by acylation with valeryl chloride to give N-[(2'-cyanobiphenyl-4-yl]methyl]-N-valeryl-L-valine ester and further by the conversion to valsartan.

WO 2007/005967 discloses the condensation of p-Bromobenzylbromide with valine methyl ester to give (S)-methyl-2-(4-bromobenzylamino)-3-methyl butanoate which on reaction with valeryl chloride to give (S)-methyl-2-(4-bromobenzyl)pentanamido)-3-methylbutanoate. (S)-methyl-2-(4-bromobenzyl)pentanamido)-3-methylbutanoate is treated with 2-(1-trityl-1H-tetrazol-5-yl)phenylboronic acid to give (S)-3-methyl-2-{pentanoyl-[2'-(1-trityl-1H-tetrazol-5-yl)biphenyl-4-ylmethyl]amino}butyric acid methyl ester and base hydrolysis to give trityl valsartan. Triltyl valsartan is treated with an acid to give valsartan.

According to WO 2007/006531 describes the reaction of metal salts of 2'-(1H-tetrazol-5-yl)-1,1'-biphenyl-4-carboxaldehyde with valine derivative under conditions of reductive amination and acylating the resulting compound with valeryl derivative to give valsartan.

WO2007/045675 discloses the imination of 4-Bromobenzaldehyde with L-valine to give an imine type schiff's base. Reduction of imine group followed by acidification and N-acylation with valerylchloride to give N-(4-bromobenzyl)-N-valeryl-L-valine.

EP 1777224 describes the condensation of p-Bromobenzaldehyde with L-valine followed by reduction with sodium borohydride to give (S)-2-(4-bromobenzyl)amino-3-methylbutyric acid. (S)-2-(4-bromobenzyl)amino-3-methyl butyric acid is treated with valerylchloride to give (S)-2-(4-bromobenzyl)-pentanoyl-amino-3-methyl butyric acid. (S)-2-(4-bromobenzyl)-pentanoyl-amino-3-methyl butyric acid is treated with 2-(2H-tetrazol-5-yl)benzene-boronic acid in tetrahydrofuran, triphenylphosphine and palladiumacetate yield valsartan.

WO 2007/054965 describes the reaction of N-[2'-cyanobiphenyl-4-yl)methyl]-L-valinemethylester oxalate salt and valeryl chloride to give N-[(2-cyanobiphenyl-4-yl)methyl]-N-pentanoyl-L-valine methylester followed by the treatment with tributyltin chloride, sodium azide and triethylamine to give valsartan.

WO2007/057919 discloses the preparation of valsartan by the hydrolysis of valsartan ester derivative in the presence of phase transfer catalyst. Valsartan ester is prepared by the treatment of N-[(2'-cyanobiphenyl-4-yl)methyl]-N-pentanoyl-L-valineester derivative with tributyl tin azide and tetrabutyl ammonium bromide.

WO 2007/071750 describes the reaction of L-valine benzyl ester tosylate and 4-(5,5-dimethyl-[1,3,2]-dioxaborinan-2-yl)benzaldehyde in triethylamine to give benzyl N-[4-(5,5-dimethyl-[1,3,2]-dioxaborinan-2-yl)phenyl-4-yl-methyl]-L-valinate which on acylation and followed by debenzylation to give N-[4-(5,5-dimethyl-[1,3,2]dioxaborinan-2-yl)phenyl-4-yl-methyl]-N-pentanoyl-L-valine. 5-(2-Bromophenyl)-1-triphenylmethyl-1H tetrazole, N-[4-(5,5-dimethyl-[1,3,2]dioxaborinan-2-yl)phenyl-4-yl-methyl]-N-pentanoyl-L-valine in a solution of Pd(Oac)$_2$ and PPh3 in tetrahydrofuran to give valsartan.

According to WO 2008/004110 L-valinemethylester hydrochloride is added to a mixture of 1-triphenylmethyl-5-[4'-(bromomethyl)biphenyl-2-yl]-tetrazole, N,N-dimethylformamide and then treated with oxalic acid to give N-[[2'-(1-triphenylmethyltetrazol-5-yl)biphenyl-4-yl]methyl]L-valine methylester oxalate. N-[[2'-(1-triphenylmethyltetrazol-5-yl)biphenyl-4-yl]methyl]-L-valine methyl ester oxalate is basified and then added valerylchloride to give N-[[2'-(1-triphenylmethyltetrazol-5-yl)biphenyl-4-yl]methyl]-N-valeryl-L-valine methyl ester. Deprotection of N-[[2'-(1-triphenylmethyl tetrazol-5-yl)biphenyl-4-yl]methyl]-N-valeryl-L-valine methylester using anhydrous acidic conditions to produce valsartan methylester followed by treating with a base to produce valsartan.

WO 2008/007391 describes a process for the preparation of valsartan which involves the conversion of N-[(2'-Cyano[1,1-biphenyl]-4-yl)methyl]-L-valine methylester to N-[[2'-(1H-tetrazol-5yl)[1,1'-biphenyl-4-yl]methyl]-L-valine in the presence of mixture of metal azide and alkyl tin halide followed by the condensation of N-[[2'-(1H-tetrazol-5yl)[1,1-b]phenyl-4-yl]methyl]-L-valine with 5-Phenylthiovaleric acid derivative to give N-(5-(phenylthio)-1-oxopentyl)-N-[[2'-(1H-tetrazol-5-yl)[1,1-biphenyl]-4-yl]methyl]-L-valine and desulfurisation with transition metal halide hydrate to give valsartan.

N-[(2'-cyano[1,1'-biphenyl]-4-yl)methyl]-L-valine benzylester of formula I shown in the specification is the key intermediate in the preparation of valsartan or a pharmaceutical acceptable salt. The intermediate is obtained by the alkylation of L-valine benzyl ester of formula:

with 4-Bromomethyl-2-cyano biphenyl of formula:

The processes describes in the prior art for the preparation of N-[(2'-cyano[1,1'-biphenyl]-4-yl)methyl]-L-valine benzylester results in the formation of an high content of by-product of formula:

as impurity. The formation of this impurity is more pronounced in the scale up batches. The impurity thus obtained is converted further in the following way as shown below during the preparation of valsartan.

Scheme:

-continued

Thus, valsartan produced by the prior art contains the impurity of formula:

The impurity thus formed is difficult to remove and it requires repeated purifications to obtain pure valsartan resulting in heavy loss of the yield of valsartan. Therefore it is required to control the formation of corresponding impurity at the source the impurity formation so that the content of the impurity at the source is at a minimum possible level and to isolate the corresponding impurity formed at the source of formation. Even though the patent publication WO 2007/032019 addresses the separation of the impurity, the separation requires the conversion of N-[(2'-cyano[1,1'-biphenyl]-4-yl)methyl]-L-valine benzylester in to the an acid addition salt, and crystallization of the acid addition salt and basifying before proceeding to the preparation of valsartan. Thus, the process involves the additional chemical reaction steps. There still requires a simple but effective process for obtaining valsartan in high purity and high yield.

Thus, there is a need for obtaining valsartan or a pharmaceutically acceptable salt in a pure form and in a better yield.

According to one object of the present invention, there is provided a process for obtaining N-[2'-cyano[1,1'-biphenyl]-4-yl)methyl]-L-valine benzyl ester substantially free of N-bis-[(2'-cyano[1,1'-biphenyl]-4-yl)methyl]-L-valine benzylester.

According to another object of the present invention there is provided free base of N-[(2'-cyano[1,1'-biphenyl]-4-yl)methyl]-L-valine benzylester substantially free of N-bis-[(2'-cyano[1,1'-biphenyl]-4-yl)methyl]-L-valinebenzylester.

N-[(2'-cyano[1,1'-biphenyl]-4-yl)methyl]-L-valine benzylester may be used for preparing valsartan or pharmaceutically acceptable salt thereof in high purity and better yield.

DETAILED DESCRIPTION OF THE INVENTION

Figure 1:
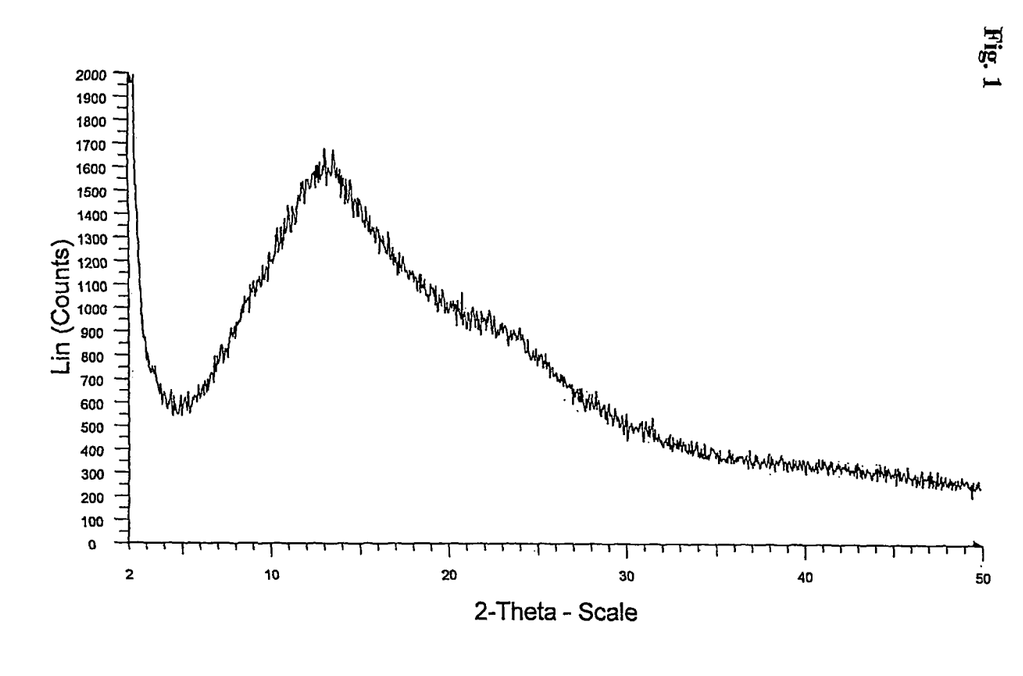
FIG. 1 is an x-ray powder diffraction spectrum of a compound of the invention.
Figure 2:
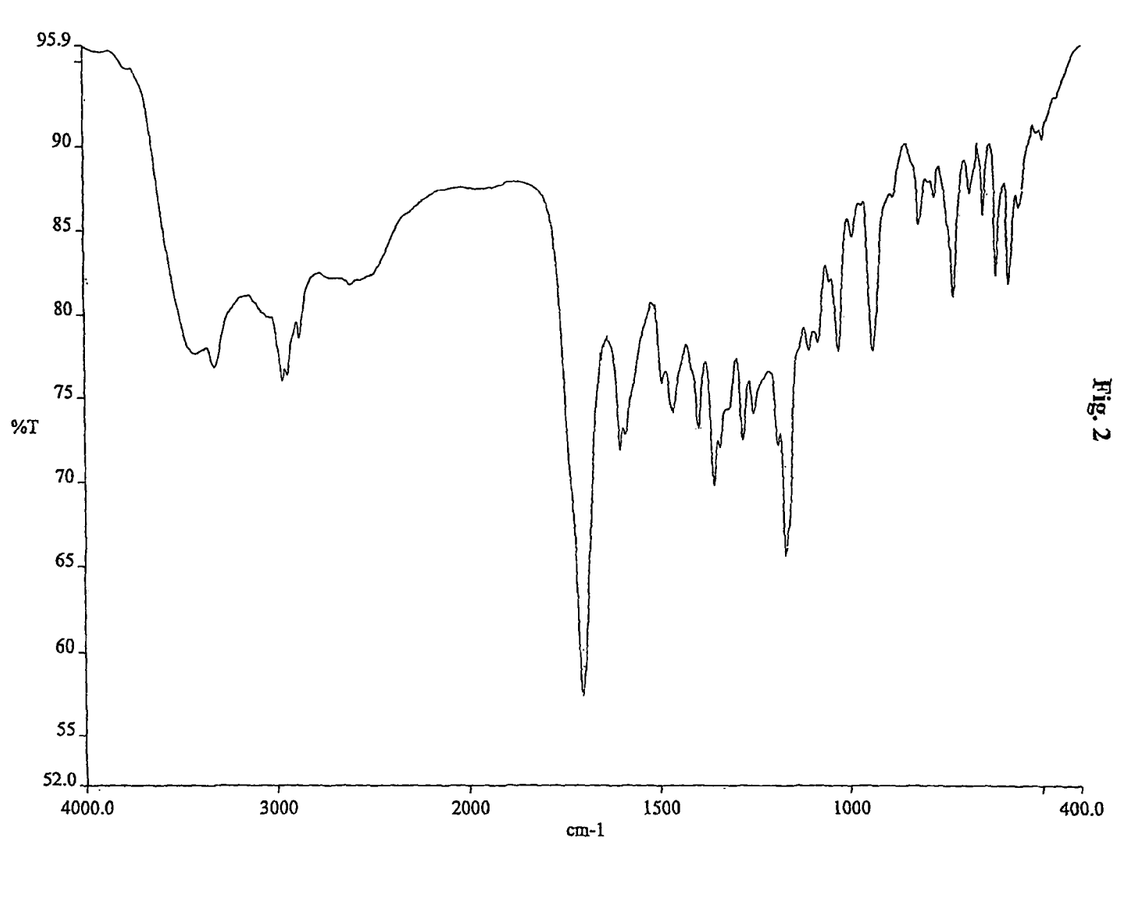
FIG. 2 is an IR spectrum of a compound of the invention.

N-[(2'-cyano[1,1-biphenyl]-4-yl)methyl]-L-valine benzylester of formula I shown in the specification is the key intermediate in the preparation of valsartan or a pharmaceutical acceptable salt. A route of synthesis for the preparation of valsartan can be represented as shown in below:

Scheme:

diisopropylethylamine | HCl

-continued

R = methyl or benzyl

↓ n-valerylchloride
diisopropylethylamine

R = methyl or benzyl

↓ tributyltin azide base ↘     ↙ Pd/C

Valsartan

According to one aspect of the present invention there is provided a process for preparing N-[(2'-cyano[1,1'-biphenyl]-4-yl)methyl]-L-valine benzyl ester of formula I or an acid addition salt substantially free of N,N-bis-[(2'-cyano[1,1'-biphenyl]-4-yl)methyl]-L-valinebenzylester of formula III which process comprises:
a) preparing a solution of L-valine benzylester in a solvent at about 40-140 deg C. in the presence of a base
b) adding a solution of 4-Bromomethyl-2-cyanobiphenyl of formula II gradually at least for 1 hour 30 minutes to the solution prepared in step (a) maintaining the temperature at about 40-140 deg C.

c) maintaining the reaction mass for at least 3 hours at about 40-140 deg C.
d) isolating the N-[(2'-cyano[1,1'-biphenyl]-4-yl)methyl]-L-valine benzylester of formula I or converting the compound of formula I into an acid addition salt and isolating as the solid.

Preferably the solvent used in the preparations of solutions in step (a) or (b) may independently be selected from ethylacetate, acetone, tetrahydrofuran, 1,4-dioxane, acetonitrile, N,N-dimethylformamide, toluene and a mixtures thereof, more preferable solvents being ethylacetate and acetone, still more preferable being ethylacetate.

Preferably the temperature maintained in step (a), (b) or (c) is about 50-120 deg C., more preferably at about 60-100 deg C., more preferably at about 70-90 deg C.

The gradual addition of the solution in step (b) may preferably be carried out for 1 hour 30 minutes to 10 hours, more preferably for 2 hours to 8 hours.

The reaction in step (c) may preferably be maintained for 3 hours to 20 hours, preferably for 4 hours to 15 hours, more preferably for 5 hours to 14 hours.

The isolation of N-[(2'-cyano[1,1'-biphenyl]-4-yl)methyl]-L-valine benzyl ester of formula I may be carried out by conventional means, optionally the compound of formula I may be converted into an acid addition salt and isolated from the reaction mass as acid addition salt by conventional means.

Preferably N-[(2'-cyano[1,1'-biphenyl]-4-yl)methyl]-L-valine benzylester of formula I may be converted into hydrochloride salt of N-[(2'-cyano[1,1'-biphenyl]-4-yl)methyl]-L-valine benzylester of formula I by adding aqueous solution of hydrochloric acid or an anhydrous hydrogen chloride.

According to another aspect of the present invention there is provided a process for purification of an acid addition salt of N-[(2'-cyano[1,1'-biphenyl]-4-yl)methyl]-L-valine benzylester which process comprises stirring the acid addition salt of N-[(2'-cyano[1,1'-biphenyl]-4-yl)methyl]-L-valine benzylester containing impurity of N,N-bis-[(2'-cyano[1,1'-biphenyl]-4-yl)methyl]-L-valinebenzylester or an acid addition salt thereof with ethylacetate and isolating the acid addition salt of N-[(2'-cyano[1,1'-biphenyl]-4-yl)methyl]-L-valine benzylester substantially free of N-bis-[(2'-cyano[1,1'-biphenyl]-4-yl)methyl]-L-valinebenzylester or an acid addition salt thereof.

The acid addition salt of N-[(2'-cyano[1,1'-biphenyl]-4-yl)methyl]-L-valine benzylester containing impurity of N,N-bis-[(2'-cyano[1,1'-biphenyl]-4-yl)methyl]-L-valine benzylester or an acid addition salt thereof may be in the form of dissolved or suspended in ethylacetate during stirring. Preferably, stirring may be performed for at least 15 minutes and more preferably 15 minutes to 4 hours.

The stirring may preferably be carried out at elevated temperatures, and more preferably under reflux.

The isolation of acid addition salt of N-[(2'-cyano[1,1'-biphenyl]-4-yl)methyl]-L-valine benzylester substantially free of N,N-bis-[(2'-cyano[1,1'-biphenyl]-4-yl)methyl]-L-valinebenzyl ester or an acid addition salt thereof from the solvent may preferably be carried out by filtration or centrifugation.

If required isolation of acid addition salt of N-[(2'-cyano[1,1'-biphenyl]-4-yl)methyl]-L-valine benzylester substantially free of N,N-bis-[(2'-cyano[1,1'-biphenyl]-4-yl)methyl]-L-valinebenzyl ester or an acid addition salt thereof from the solvent may be carried out by crystallization. The crystallization may be carried out by conventional means such as cooling, partial or complete removal of solvent or seeding; or combination thereof.

The preferable acid addition salt is a mineral acid salt, more preferable acid addition salt is hydrochloride salt or sulfuric acid salt and still more preferable salt being hydrochloride salt.

According to another aspect of the present invention there is provided free base of N-[(2'-cyano[1,1'-biphenyl]-4-yl)methyl]-L-valine benzylester of formula I or a mineral acid addition salt thereof substantially free of N-bis-[(2'-cyano[1,1'-biphenyl]-4-yl)methyl]-L-valinebenzyl ester or an mineral acid addition salt thereof. Preferably, the free base of N-[(2'-cyano[1,1'-biphenyl]-4-yl)methyl]-L-valine benzylester or a mineral acid addition salt thereof substantially free of N-bis-[(2'-cyano[1,1'-biphenyl]-4-yl)methyl]-L-valinebenzyl ester or a mineral acid addition salt thereof is in the form of isolated solid. The more preferable mineral acid addition salt is hydrochloride salt.

N-[(2'-cyano[1,1'-biphenyl]-4-yl)methyl]-L-valine benzylester substantially free of N-bis-[(2'-cyano[1,1'-biphenyl]-4-yl)methyl]-L-valinebenzyl ester refers to N-[(2'-cyano[1,1'-biphenyl]-4-yl)methyl]-L-valine benzylester containing N-bis-[(2'-cyano[1,1'-biphenyl]-4-yl)methyl]-L-valinebenzyl ester in less than 15% of N-bis-[(2'-cyano[1,1'-biphenyl]-4-yl)methyl]-L-valinebenzyl ester, preferably in less than 10% of N-bis-[(2'-cyano[1,1'-biphenyl]-4-yl)methyl]-L-valinebenzyl ester of and still more preferably in less than 5%.

N-[(2'-cyano[1,1'-biphenyl]-4-yl)methyl]-L-valine benzylester of formula I or an acid addition salt thereof obtained according to the process of the present invention may be used to prepare Valsartan or pharmaceutically acceptable salt by the known procedures.

The invention will now be further describes by the following examples, which are illustrative rather than limiting.

EXAMPLES

Example 1

Acetone (300 ml) is added to L-valine benzylester (100 gm) and sodium carbonate (92 gm) at room temperature, stirred for 15 minutes and heated to reflux. 4-Bromomethyl-2-cyanobiphenyl (114 gm) is dissolved in acetone (500 ml) and is added to the L-valine benzylester solution prepared above slowly for 4 hours at reflux. Maintained under reflux for 15 hours. Distilled off the solvent completely under vacuum below 50 deg C. water (600 ml) is added the residue obtained at room temperature. The reaction mass is extracted with methylenedichloride (300 ml), washed the organic layer with water (500 ml) and further washed with 10% sodium chloride solution (300 ml). Organic layer is dried over sodium sulfate and distilled under vacuum below 50 deg C. isopropanol (500 ml) is added to the residue at room temperature followed by the addition of isopropanol saturated with hydrogenchloride (100 ml) for 1 hour at room temperature till the pH is reached 1.5-2. Stirred for 2 hours at room temperature, cooled to 5 deg C., maintained for 1 hour and filtered to obtain N-[(2'-cyano[1,1'-biphenyl]-4-yl)methyl]-L-valine benzylester hydrochloride (yield 160 gm; HPLC purity: 99%). Content of N,N-bis-[(2'-cyano[1,1'-biphenyl]-4-yl)methyl]-L-valinebenzylester impurity: 0.1%.

Example 2

L-valinebenzylester (100 gm), acetone (600 ml), 4-Bromomethyl-2-cyano biphenyl (130 gm) and sodium carbonate (98 gm) are taken in a round bottomed flask and raised the mass temperature to reflux and maintained for 15 hours. Distilled off the solvent under vacuum at less than 50 deg C., water (600 ml) is added at room temperature. The reaction mass is extracted with methylene dichloride (300 ml), washed the organic layer with water (500 ml) and further washed with 10% sodium chloride solution (300 ml). Organic layer is dried over sodium sulfate and distilled under vacuum at less than 50 deg C. Ethylacetate (500 ml) is added to the residue at room temperature followed by the addition of isopropanol saturated with hydrogenchloride (100 ml) for 1 hour at room temperature till the pH is reached 1.5-2. Stirred for 2 hours at room temperature, cooled to 5 deg C., maintained for 1 hour, filtered to obtain N-[(2'-cyano[1,1'-biphenyl]-4-yl)methyl]-L-valine benzylester hydrochloride (Yield: 150 gm). Content of N,N-bis-[(2'-cyano[1,1'-biphenyl]-4-yl)methyl]-L-valinebenzyl ester impurity: 15.2%.

Purification:

Ethylacetate (1000 ml) is added to N-[(2'-cyano[1,1'-biphenyl]-4-yl)methyl]-L-valinebenzylester hydrochloride (100 gm) and refluxed for 30 minutes. Cooled to room temperature, stirred for 2 hours, further cooled to 10 deg C., stirred for 1 hour, filtered, washed with ethylacetate (50 ml) and dried up to a constant weight to obtain N-[(2'-cyano[1,1'-biphenyl]-4-yl)methyl]-L-valinebenzylester hydrochloride (yield: 80 gm; HPLC purity: 99.3%). Content of N,N-bis-[(2'-cyano[1,1'-biphenyl]-4-yl)methyl]-L-valinebenzylester impurity is not detected by HPLC.

Example 3

Ethylacetate (250 ml) is added to L-valinebenzylester (100 gm) and sodium carbonate (91 gm) at room temperature, stirred for 15 minutes and heated to 70 deg C. 4-Bromomethyl-2-cyanobiphenyl (114 gm) is dissolved in ethylacetate (1700 ml) and was added to L-valine benzylester solution slowly for 4 hours at 70 deg C. Maintained under reflux for 11 hours. The mass is cooled to room temperature and water (1000 ml) is added. Stirred for 10 minutes, separated the layers and the organic layer is washed with water (1000 ml) and then with 10% aqueous sodium chloride solution (1000 ml). The organic layer is dried over sodium sulfate and distilled off the solvent under vacuum. Ethylacetate (600 ml) is added to the residue at room temperature. Cooled to 5 deg C. and the pH is adjusted to 1.5-2 with isopropanol saturated with hydrogen chloride. Stirred for 2 hours 30 minutes at 5 deg C. and filtered the solid to obtain N-[(2'-cyano[1,1'-biphenyl]-4-yl)methyl]-L-valinebenzylester hydrochloride. (Yield: 159 gm; HPLC purity: 98.5%). Content of N,N-bis-[(2'-cyano[1,1'-biphenyl]-4-yl)methyl]-L-valine benzylester impurity: 0.2%.

Example 4

Ethylacetate (600 ml) is added to L-valinebenzylester (262 gm) and sodium carbonate (240 gm) at room temperature, stirred for 15 minutes and heated to mild reflux. 4-Bromomethyl-2-cyanobiphenyl (300 gm) is dissolved in ethyl acetate (4500 ml) and was added to L-valine benzylester solution slowly for 4 hours at 70 deg C. Maintained under reflux for 12 hours. The reaction mass is cooled to room temperature and water (3000 ml) is added. Stirred for 10 minutes, separated the layers and the organic layer is washed with water (3000 ml) and then with 10% aqueous sodium chloride solution (3000 ml). The organic layer is dried over sodium sulfate and distilled completely under vacuum. Ethyl acetate (1500 ml) is added to the residue at room temperature. Cooled to 5 deg C. and the pH is adjusted to 1.5-2 by passing hydrogen chloride gas. Stirred for 2 hours at 5 deg C. and filtered the solid to obtain N-[(2'-cyano[1,1-biphenyl]-4-yl)methyl]-L-valinebenzylester hydrochloride. (Yield: 460 gm; HPLC purity: 99.2%). N,N-bis-[(2'-cyano[1,1'-biphenyl]-4-yl)methyl]-L-valinebenzylester impurity is not detected.

Example 5

Ethylacetate (150 ml) is added to L-valinebenzylester (42 gm) and sodium carbonate (46 gm) at room temperature, stirred for 15 minutes and heated to 70 deg C. 4-Bromomethyl-2-cyanobiphenyl (50 gm) is dissolved in ethylacetate (800 ml) and is added to L-valine benzylester solution slowly for 4 hours at 70 deg C. Maintained under reflux for 12 hours. The mass is cooled to room temperature and water (500 ml) is added. Stirred for 10 minutes, separated the layers and the organic layer is washed with water (500 ml) and then with 10% aqueous sodium chloride solution (500 ml). The organic layer is dried over sodium sulfate and distilled completely under vacuum. Ethylacetate (300 ml) is added to the residue at room temperature. Cooled to 10 deg C. and the pH is adjusted to 1.5-2 by concentrated hydrochloric acid. Stirred for 2 hours 30 minutes at 10 deg C. and filtered the solid to obtain N-[(2'-cyano[1,1'-biphenyl]-4-yl)methyl]-L-valinebenzylester hydrochloride. (Yield: 65 gm; HPLC purity: 98.9%). Content of N,N-bis-[(2'-cyano[1,1'-biphenyl]-4-yl)methyl]-L-valinebenzyl ester impurity: 0.1%.

Example 6

N-[(2'-cyano[1,1'-biphenyl]-4-yl]methyl]-L-valinebenzylester hydrochloride (100 gm), methylenedichloride (800 ml), sodiumcarbonate (80 gm) are taken in a round bottomed flask at room temperature and cooled to 0 deg C. The solution of valerylchloride (40 gm) in methylenedichloride (200 ml) is added to the reaction flask for about 1 hour 30 minutes at 0 deg C. and maintained for 30 minutes. Heated to mild reflux, maintained for 3 hours, washed with water (2×500 ml). The separated organic layer is washed with 10% aqueous sodiumchloride solution, dried and distilled off the solvent under reduced pressure to obtain N-[(2'-Cyano[1,1-biphenyl]-4-yl)methyl]-n-valeryl-L-valine benzyl ester as a brownish oily mass (yield: 100 gm; HPLC: 96.5%).

Example 7

N-[(2'-cyano[1,1'-biphenyl]-4-yl)methyl]-L-valinebenzylester hydrochloride (500 gm) is added to methylenechloride (3000 ml) and then sodium carbonate (400 gm) is added. The reaction mass is cooled to 5 deg C., valerylchloride (200 gm) in methylenechloride (2000 ml) is added drop wise for 2 hours 30 minutes at −5 to 0 deg C. and the temperature of the reaction mass is then raised to room temperature. Maintained for 2 hours at room temperature. The mass is washed with water (5000 ml) and the methylenechloride (625 ml) layer is washed with 10% aqueous sodium chloride solution (2500 ml). Methylenechloride layer is dried over sodium sulfate and distilled off the solvent under vacuum below 50 deg C. to obtain N-[(2'-Cyano[1,1'-biphenyl]-4-yl)methyl]-n-valeryl-L-valine benzyl ester as a brownish oily mass (yield: 550 gm; HPLC purity: 97.2%).

Example 8

N-[(2'-cyano[1,1'-biphenyl]-4-yl]methyl]-N-valeryl-L-valinebenzylester (100 gm), o-Xylene (800 ml), tributyl tinchloride (200 gm) and sodium azide (40 gm) are taken into round bottomed flask at room temperature, heated to reflux and maintained at reflux for 24 hours. The reaction mass is cooled to room temperature, passed over celite bed, washed with o-Xylene (100 ml) and completely distilled under vacuum at less than 90 deg C. Methanol (100 ml) is added and distilled under vacuum. Added methanol (300 ml) and cooled to room temperature. Water (1000 ml), n-hexane (800 ml) are added to the reaction mass at room temperature and the pH is adjusted to 12 with sodium hydroxide solution at room temperature. Stirred for 10 minutes, separated the layers and the aqueous layer is washed with n-hexane. Methylenechloride is added to the aqueous layer and the pH is adjusted to 1.5 with aqueous hydrochloric acid at room temperature. Separated the layers and aqueous layer is extracted with methylenedichloride. Total organic layer is washed with water and then with sodium chloride, dried and distilled off under vacuum at below 60 deg C. to obtain N-[(2'-Cyano[1,1'-biphenyl]-4-yl) methyl]-n-valeryl-L-valine benzyl ester as a brownish oily mass (yield: 100 gm; HPLC purity: 92.3%).

Example 9

Sodium azide (120 gm), water are taken in a round bottomed flask and cooled to 0 deg C. Tributyltinchloride (510 gm) is added dropwise at 0 deg C. for 1 hour 30 minutes. Maintained for 2 hours at 0 deg C. The temperature is raised to room temperature. o-Xylene (1200 ml) is added and the layers are separated. The aqueous layer is extracted with o-Xylene (400 ml) and the aqueous layer is discarded. The organic layers are combined and washed with 10% aqueous sodium chloride solution. The o-Xylene layer is taken in a round bottom flask and added N-[(2-Cyano[1,1'-biphenyl]-4-yl)methyl]-n-valeryl-L-valine benzylester (200 gm). Heated to reflux for 25 hours. The reaction mass is cooled to 5 deg C., the pH is adjusted to 1.5 using hydrochloric acid and stirred for 4 hours. Cyclohexane (1200 ml) is added and then seeded with the N-(1-oxopentyl)-N-[[(2'-(1H-tetrazol-5-yl)-1,1'-biphenyl]-4-yl]methyl]-L-valinebenzylester. Stirred for 24 hours at room temperature, cooled to 0 deg C. and then stirred for 3 hours. Filtered the N-(1-oxopentyl)-N-[[(2'-(1H-tetrazol-5-yl)-1,1'-biphenyl)-4-yl]methyl]-L-valine benzylester and dried. The solid is taken in cyclohexane (1000 ml), stirred for 1 hour at 50 deg C., cooled to 25 deg C. and stirred for 2 hours 30 minutes. Stirred for 1 hour 30 minutes at 0 deg C. Filtered and dried to obtain N-(1-oxopentyl)-N-[[(2'-(1H-tetrazol-5-yl)-1,1'-biphenyl]-4-yl]methyl]-L-valinebenzyl ester (yield: 170 gm; purity: 99.2%).

Example 10

A solution of 100 gm of N-(1-oxopentyl)-N-[[(2'-(1H-tetrazol-5-yl)-1,1'-biphenyl)-4-yl]methyl]-L-valinebenzylester in 1000 ml ethylacetate, acetic acid (1000 ml), ammonium formate (5 gm) and sulfuric acid (2 ml) is hydrogenated at 30 deg C. with 15 gm of 5% Pd—C until the completion of reaction. Reaction mass is passed over a celite bed, washed with acetic acid (50 ml), distilled off the solvent under vacuum at below 60 deg C. and co-distilled using methanol (100 ml). Added methanol (200 ml), water (800 ml) and n-hexane (400 ml) to the reaction mass and basified with 3N aqueous sodium hydroxide solution at room temperature. Separated the layers and the aqueous layer is washed with n-hexane (400 ml). Ethylacetate (800 ml) is added to the aqueous layer and the pH of the reaction mass is adjusted to 1 to 1.5 with 4N hydrochloric acid at room temperature. Stirred for 10 minutes, separated the layers, aqueous layer is extracted with ethylacetate (400 ml). Organic layers are combined, washed with water (800 ml), 10% aqueous sodium chloride solution (800 ml), dried and concentrated under vacuum at below 60 deg C. Ethylacetate (200 ml) and diisopropylether (600 ml) are added and the solid is separated. Stirred for 4 hours at room temperature, cooled to 0 deg C., maintained for 1 hour and filtered (47.5 gm of 99.5% pure valsartan). Content of N,N-bis-[[(2'-(1H-tetrazol-5-yl)-1,1'-biphenyl)-4-yl]methyl]-L-valine impurity is not detected by HPLC.

Example 11

A solution of 100 gm of N-(1-oxopentyl)-N-[[(2'-(1H-tetrazol-5-yl)-1,1'-biphenyl)-4-yl]methyl]-L-valinebenzylester in 1000 ml ethylacetate is hydrogenated at 30 deg C. with 15 gm of 5% Pd—C until the hydrogen uptake is ceased. The mass over celite bed and filtrate is collected. Added 10% sodium bicarbonate solution (500 ml). Stirred for 20 minutes and the layers are separated. Collected the aqueous layer and washed with ethylacetate (500 ml). Added ethylacetate (300 ml) to the aqueous layer and the pH is adjusted to 1.5-2 with 2N hydrochloric acid solution. Stirred for 15 minutes and separated the layers. The aqueous layer is extracted with ethylacetate (250 ml), ethylacetate layers are combined and washed with water (500 ml) and then with 10% aqueous sodium chloride solution (500 ml). Ethylacetate layer is dried over sodium sulfate and distilled under vacuum below 50 deg C. Ethylacetate (200 ml) is added to the residue while hot. Stirred for 5 minutes to obtain clear solution. Cyclohexane (200 ml) is added at room temperature, stirred for 15 minutes. Cyclohexane (400 ml) is added to the above mass at room temperature. Stirred the mass at room temperature for 4 hours. Cooled to 5 deg C. and then stirred for 1 hour 30 minutes. Filtered the solid, washed with a mixture of ethylacetate (20 ml) and cyclohexane (80 ml) and dried to give 70 gm of 99.9% pure valsartan. Content of N,N-bis-[[(2'-(1H-tetrazol-5-yl)-1,1'-biphenyl)-4-yl]methyl]-L-valine impurity is not detected by HPLC.

Example 12

Valsartan benzyl ester (100 gm), water (800 ml) and sodium hydroxide (50 gm) are mixed and stirred for dissolution. The solution is heated to 65° C. and maintained for 2 hours 30 minutes at 60° C. to 65° C. The reaction mass is cooled to 25° C. and then washed with n-heptane (800 ml). The pH of the separated aqueous layer is adjusted to 2.0 by adding dilute hydrochloric acid at 20° C. to 25° C. Then the aqueous layer is extracted with methylene dichloride (1100 ml). Methylene dichloride layer is washed with water (1600 ml) and then with 10% sodium chloride solution (300 ml). Methylene dichloride layer is dried using sodium sulfate and then distilled under vacuum at 60° C. to give 90 gm of residue. The residue is added to a mixture of ethyl acetate (235 ml) and diisopropyl ether (235 ml) and heated to reflux. Then the reaction mass is treated with activated charcoal, filtered through hi-flow bed and washed with diisopropyl ether (80 ml) and ethyl acetate (80 ml) at 50° C. The clear filtrate is cooled to 25° C. and stirred for 2 hours at 25° C. to 30° C. Then a further quantity of diisopropyl ether (720 ml) is added, maintained for 10 hours at 20° C. to 25° C., cooled to 0° C. and maintained for 2 hours at 0° C. to 5° C. Then filtered the contents, washed with chilled diisopropyl ether (100 ml) and dried to give 50 gm of 99.7% pure valsartan.

The invention claimed is:

1. A process for preparing N-[(2-cyano[1,1'-biphenyl]-4-yl)methyl]-L-valine benzyl ester of formula I or an acid addition salt substantially free of N,N-bis-[(2'-cyano[1,1'-biphenyl]-4-yl)methyl]-L-valine benzyl ester of formula III

I

III which process comprises: a) preparing a solution of L-valine benzyl ester in a solvent at about 40-140° C. in the presence of a base b) adding a solution of 4-Bromomethyl-2-cyanobiphenyl of formula II gradually at least for 1 hour 30 minutes to the solution prepared in step (a) maintaining the temperature at about 40-140° C.

II c) maintaining the reaction mass for at least 3 hours at about 40-140 deg C. d) isolating the N-[(2'-cyano[1,1'-biphenyl]-4-yl)methyl]-L-valine benzyl ester of formula I or converting the compound of formula I into an acid addition salt and isolating as the solid.

2. The process according to claim 1, the addition of the solution in step (b) is carried out for 1 hour 30 minutes to 10 hours.

3. The process according to claim 2, the addition of the solution in step (b) is carried out for 2 hours to 10 hours.

4. The process according to claim 1, the solvent used in the preparations of solutions in the step (a) or (b) is selected from ethylacetate, acetone, tetrahydrofuran, 1,4-dioxane, acetonitrile, N,N-dimethylformamide, toluene and a mixtures thereof.

5. The process according to claim 4, the solvent is selected from ethylacetate and acetone.

6. The process according to claim 5, the solvent is selected from ethylacetate.

7. The process according to claim 1, the temperature maintained in step (a), (b), (c) is about 50-120° C.

8. The process according to claim 7, the temperature maintained in step (a), (b) and (c) is about 70-90° C.

9. The process according to claim 1, N-[(2'-cyano[1,1'-biphenyl]-4-yl)methyl]-L-valine benzyl ester is converted in to hydrochloride salt of N-[(2'-cyano[1,1'-biphenyl]-4-yl)methyl]-L-valine benzyl ester and then isolated as solid.

10. A process for purification of an acid addition salt of N-[(2'-cyano[1,1-biphenyl]-4-yl)methyl]-L-valine benzyl ester which process comprises stirring the acid addition salt of N-[(2'-cyano[1,1'-biphenyl]-4-yl)methyl]-L-valine benzyl ester containing impurity of N,N-bis-[(2'-cyano[1,1'-biphenyl]-4-yl)methyl]-L-valine benzyl ester or an acid addition salt thereof with ethylacetate and isolating the acid addition salt of N-[(2'-cyano[1,1'-biphenyl]-4-yl)methyl]-L-valine benzyl ester substantially free of N-bis-[(2'-cyano[1,1'-biphenyl]-4-yl)methyl]-L-valine benzyl ester or an acid addition salt thereof.

11. The process according to claim 10, the acid addition salt of N-[(2'-cyano[1,1'-biphenyl]-4-yl)methyl]-L-valine benzyl ester is hydrochloride salt.

* * * * *